United States Patent [19]
Tu et al.

[11] Patent Number: 5,989,248
[45] Date of Patent: Nov. 23, 1999

[54] MEDICAL DEVICE AND METHODS FOR TREATING TISSUES

[76] Inventors: Hosheng Tu; Lily Chen Tu, both of 2151 Palermo, Tustin, Calif. 92782

[21] Appl. No.: 09/056,899

[22] Filed: Apr. 7, 1998

[51] Int. Cl.⁶ .................................................... A61B 17/39
[52] U.S. Cl. ............................................ 606/41; 607/101
[58] Field of Search ................... 606/41, 45–51; 607/96, 98–102, 134

[56] References Cited

U.S. PATENT DOCUMENTS

| | | | |
|---|---|---|---|
| 4,985,030 | 1/1991 | Melzer et al. | 606/51 |
| 5,224,462 | 7/1993 | Delahuerga et al. | 606/42 |
| 5,290,286 | 3/1994 | Parins | 606/50 |
| 5,456,662 | 10/1995 | Edwards et al. | |
| 5,460,626 | 10/1995 | Krespi | 606/1 |
| 5,460,629 | 10/1995 | Shlain et al. | 606/46 |
| 5,505,728 | 4/1996 | Ellman et al. | 606/39 |
| 5,571,100 | 11/1996 | Goble et al. | 606/41 |
| 5,599,346 | 2/1997 | Edwards et al. | 606/41 |
| 5,688,266 | 11/1997 | Edwards et al. | 606/31 |

*Primary Examiner*—Linda C. M. Dvorak
*Assistant Examiner*—Roy Gibson

[57] ABSTRACT

A medical device for treating the uvula or reducing the mass of cellular tissues, wherein a plurality of elongate tubular shafts comprises at least one electrode disposed at its distal end portion of each shaft, a RF energy generating means, and a means for generating vibration at the distal section of the tubular element to effect the ablation and the pressure therapy, with an optional vibrational massage therapy for the tissues.

10 Claims, 10 Drawing Sheets

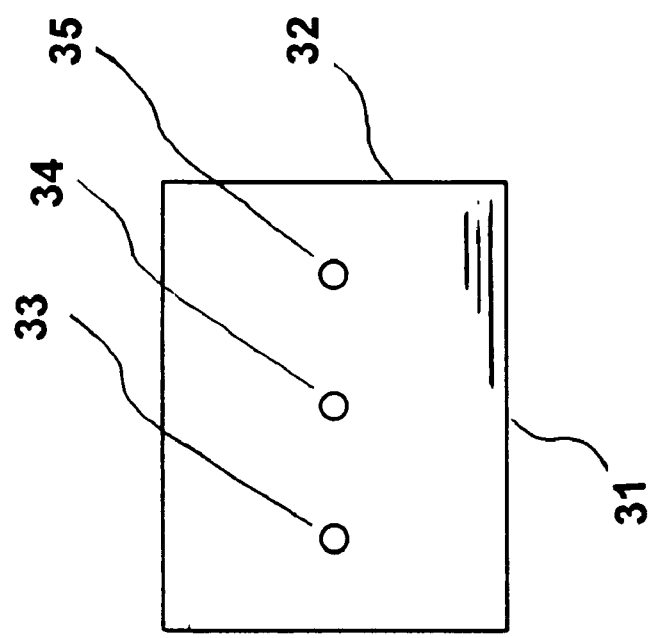
FIG. 5-B
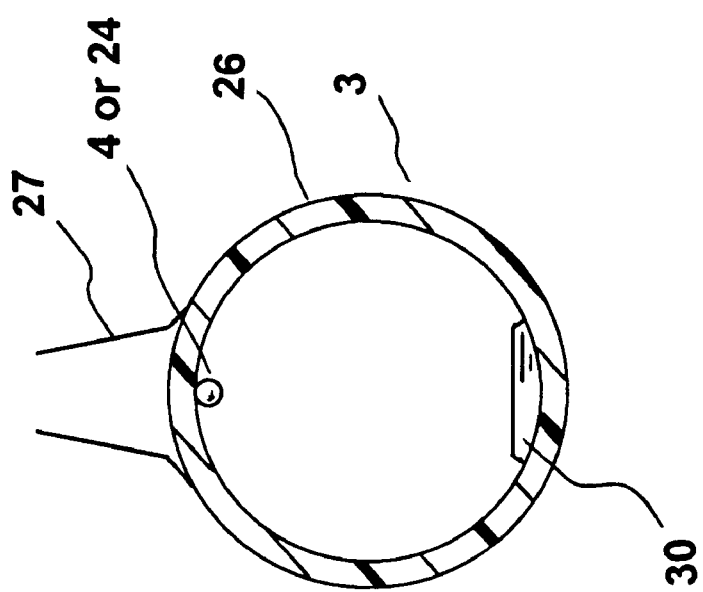
FIG. 5-A

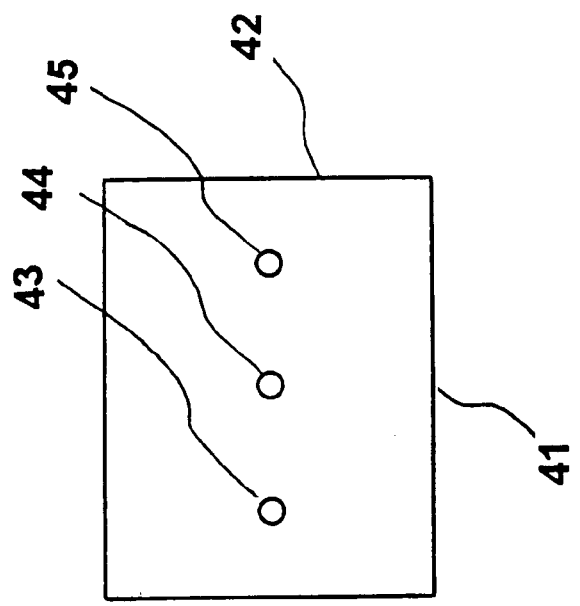
FIG. 6-B
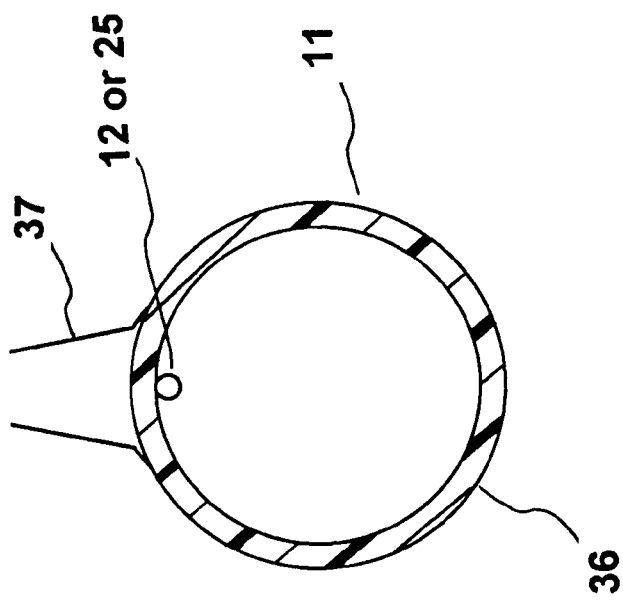
FIG. 6-A

MEDICAL DEVICE AND METHODS FOR TREATING TISSUES

The present invention generally relates to an improved medical device and methods for treating tissues, and more particularly, to such a medical device and methods for treating the uvular tissues and/or polyps in a patient by delivering RF energy to the lesion sites in association with pressure therapy.

BACKGROUND OF THE INVENTION

The methods of the destruction of cellular tissues in situ has been used in the treatment of many diseases, or as an adjunct to surgical removal procedures. One method used requires heating the tissues, and causing them to shrink and tighten. It is often less traumatic than surgical procedures and may be the only alternative method, wherein other procedures are unsafe. Ablative treatment devices have an advantage because of the use of a destructive energy that is rapidly dissipated and reduced to a non-destructive level by conduction and convection, to forces of circulating fluids and other natural processes.

Devices using microwave energy, radiofrequency energy, ultrasonic energy, cryogenic means, laser energy, and tissues destructive substances have been used to destroy malignant, benign, and other types of cells and tissues from a wide variety of anatomic sites and organs. Tissues treated include isolated carcinoma masses and, more specifically, organs such as the prostate, glandular and stromal nodules characteristic of benign prostate hyperplasia. These devices typically include a catheter or cannula which is used to carry a radiofrequency electrode or microwave energy antenna, through a duct, to the area of treatment, and applying energy diffusively through the duct wall into the surrounding tissues in the targeted directions.

Of particular interest to the present invention are RF therapeutic protocols, which have been proven to be highly effective when used by electrophysiologists for the treatment of tachycardia; by neurosurgeons for the treatment of Parkinson's disease; and by neurosurgeons and anesthetists for other RF procedures such as Gasserian ganglionectomy for trigeminal neuralgia and percutaneous cervical cordotomy for intractable pains. Radiofrequency treatment, which exposes a patient to minimal side effects and risks, is generally performed after first locating the tissue sites for treatment. Radiofrequency energy, when coupled with a temperature control mechanism, can be supplied precisely to the device-to-tissues contact site to obtain the desired temperature for creating a lesion.

To be more efficient in RF energy ablation, an electrode with a vibration capability can be used to simultaneously deliver the massage therapy to the target tissues. The electric toothbrush with vibration has been disclosed in the following patents: Suyama in U.S. Pat. No. 4,944,296, Ng in U.S. Pat. No. 5,283,921, Hwang in U.S. Pat. No. 5,381,576, Okada in U.S. Pat. No. 5,421,726, Mei in U.S. Pat. No. 5,617,603, and Hahn in U.S. Pat. No. 5,651,157. All the above patents disclose the advantage of an electric toothbrush with vibration. However, they do not teach using an ablation electrode with vibration capability to create a lesion in the tissues for therapeutic purpose.

On the other hand, Imran in U.S. Pat. No. 5,281,218 entitled "Catheter having needle electrode for radiofrequency ablation" teaches a method using a needle electrode that is attached onto a catheter for radiofrequency ablation. Though a needle-like electrode is beneficial to ablate a tissues point for deep lesion, it is not disclosed that the particular needle electrode could possibly combine pressure therapy for proper contact with the target tissues. The "pressure therapy" is defined in this invention as the application of significant pressure onto the tissues by a medical device.

Edwards et al. in U.S. Pat. No. 5,456,662 entitled "Method for reducing snoring by RF ablation of the uvula" teaches a medical ablation method for reducing snoring wherein a flexible RF electrode wire is inserted into the uvula and RF energy is applied to the uvula tissues to cause internal lesions. Edwards et al. does not disclose a catheter to ablate tissues, having the capability for simultaneously delivering radiofrequency energy and pressure therapy.

Therefore, there is a need for an improved medical device and methods using the radiofrequency energy to treat uvular, polyps, or tumors, while applying pressure and/or vibrational massage therapy.

SUMMARY OF THE INVENTION

In general, it is an object of the present invention to provide a method and an improved medical device for generating heat, to treat the uvula or other cellular tissues. It is another object of the present invention to provide a medical device so that vibrational massage therapy can be applied to the uvula site, or the targeted cellular tissues, for intimate contact. It is another object of the present invention to provide a method and a device for monitoring the temperature of the medical device, and to control the temperature by utilizing a temperature control mechanism and/or algorithm. The location of the temperature sensor means is preferably at the proximity of the electrode means of the medical device. It is still another object of this invention to provide a method and a device for treating uvula or cellular tissues in a patient by applying significant pressure to the tissues.

Briefly, heat is generated by supplying a suitable energy source to a device, that is comprised of a plurality of electrode means, in contact with the body tissues. A suitable energy source may consist of radiofrequency energy, microwave energy, ultrasonic energy, alternating current energy, or laser energy. The energy can be applied to the uvula or cellular tissues through the electrode means. A DIP (dispersive indifferent pad) type pad or electrode, that contacts the patient, is connected to the Indifferent Electrode Connector on the RF generator. When using an alternating current outlet, the generator should be grounded to avoid electrical interference. Heat is controlled by the power of the RF energy delivered and by the delivery duration. The standard RF energy generator means, and its applications through the electrode means, to a patient are well known for those who are skilled in the art.

In an optional embodiment, means for generating vibration at the distal section comprises a motor mounted in the cavity of the handle, which has a rotatable motor shaft, an elongated connecting shaft having a first end, to which the electrode is connected, and a second end connected to the handle, a weight eccentrically mounted on the motor shaft with respect to the motor shaft axis, so as to rotate eccentrically, so that when the motor shaft rotates, the electrode vibrates.

In one embodiment, the device comprises a plurality of electrode means, wherein the electrode means is composed of a slidable clamp-type that is meant to slide, longitudinally, on a shaft or bar. The electrodes clamp the targeted tissue from the tissue's opposite sides with proper pressure. The electrode means is generally selected from the group of sliding head bar clamp fixtures, deep throat bar clamp fixtures, threadless bar clamp fixtures, or the like.

In one optional embodiment, the device is leak-proof so that the therapeutic agent, in either fluid phase or gel phase, can be forced under a positive pressure to flow inside the lumen of the medical device from its proximal end to the distal end. The fluid is vented through an optional opening at the proximity of the electrode to effect the therapeutic purpose.

The method and medical device of the present invention has several significant advantages over other known systems or techniques to treat the uvula or polyps. In particular, the device system comprising the electrode means, using RF energy as a heat source, in this invention and simultaneously applying pressure therapy to the tissues, results in a more efficient therapeutic effect, which is highly desirable in its intended application on the uvula or on other medical ablation applications.

BRIEF DESCRIPTION OF THE DRAWINGS

Additional objects and features of the present invention will become more apparent and the invention itself will be best understood from the following Detailed Description of Exemplary Embodiments, when read with reference to the accompanying drawings.

FIG. 5A is an end view B—B of the first electrode means of FIG. 5.

FIG. 5B is a transverse view C—C of the first electrode means of FIG. 5.

FIG. 6A is a front view D—D of the second electrode means of FIG. 6.

FIG. 6B is a transverse view E—E of the second electrode means of FIG. 6.

DETAILED DESCRIPTION OF EXEMPLARY EMBODIMENTS

Figure 1:
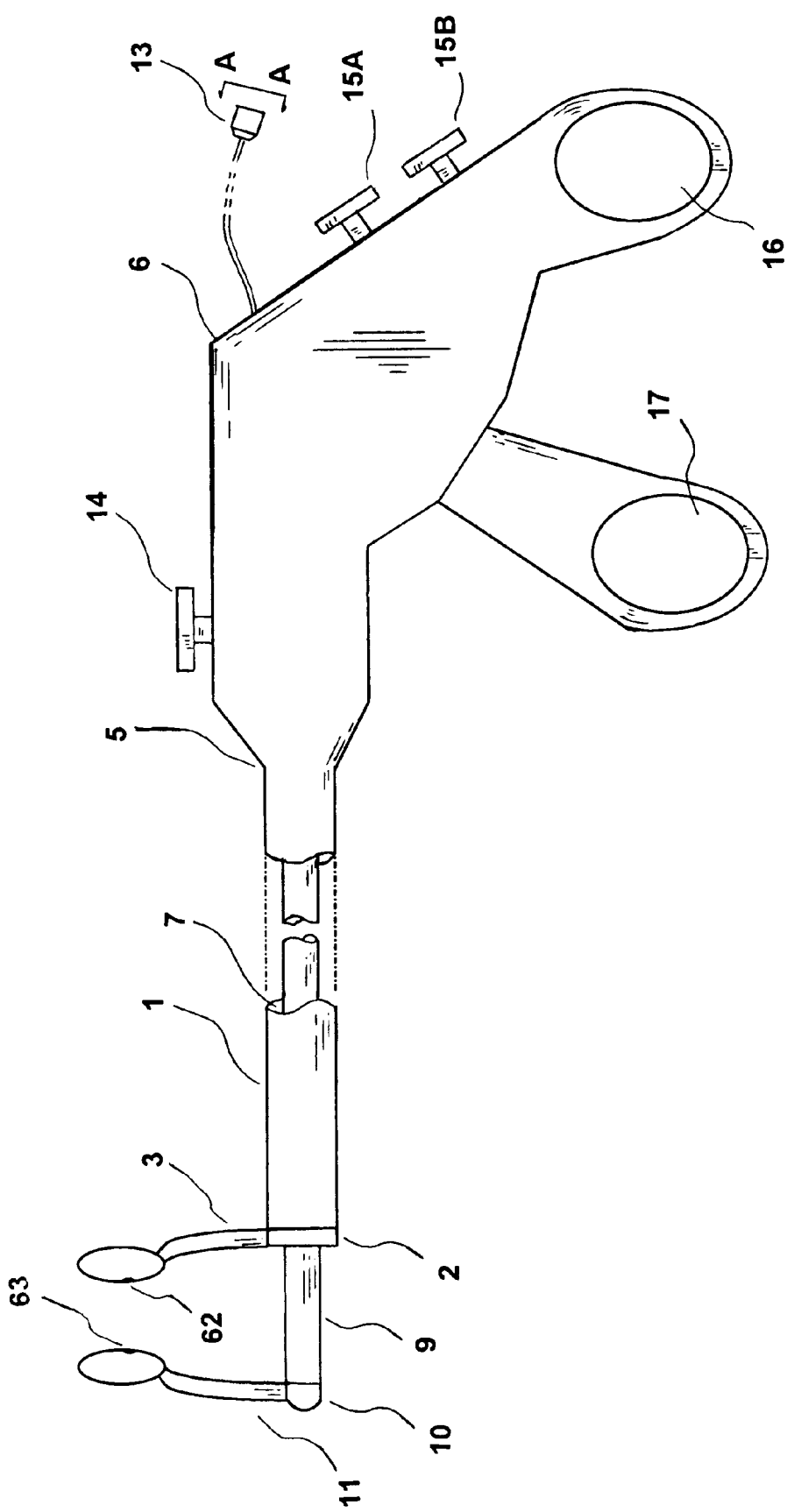
FIG. 1 is an over-all view of the medical device, comprising a plurality of electrode means having a clamp-type fixture, constructed in accordance with the principles of the present invention.

Referring to FIGS. 1 to 8, what is shown is an embodiment of the medical device system, comprising simultaneously applying radiofrequency energy and applying a pressure therapy to treat the uvula, polyps, or other cellular tissues of a patient. As shown in FIG. 1, the medical device in the form of an elongate tubular assembly comprises a first elongate tubular shaft 1, on which thereof a first electrode means 3 is mounted on a distal end portion 2, an electrical conductor 4 passing through the shaft 1 and connected to the first electrode means 3, and mounted on a proximal end portion 5 of the shaft 1 to a handpiece 6 of the device, wherein the first elongate tubular shaft 1 has at least a lumen 7 extending between the distal end portion 2 and the proximal end portion 5, and wherein the handpiece 6 has a cavity 8. A second elongate tubular shaft 9 is located within the lumen 7 of the first elongate tubular shaft 1, the second elongate tubular shaft 9, on which thereof a second electrode means 11 is mounted on a distal end portion 10, an electrical conductor 12 passing through the shaft 9 and connected to the second electrode means 11, and mounted on a proximal end portion of the shaft 9 to the handpiece 6 of the device, wherein the second elongate tubular shaft 9 is moveable longitudinally relative to the first elongate tubular shaft 1. A connector 13 is connected to the proximal end of the handpiece 6. A locking mechanism 14 is positioned at a convenient location on the handpiece 6 to lock the second elongate tubular shaft 9 in relation to the first elongate tubular shaft 1. The RF energy is supplied from an external RF energy generating means to either the first electrode means 3, the second electrode means 11, or to both electrode means through electrical conductors 4 and/or 12. One on-off control knob 15A or 15B is used to control each of the RF energy deliveries to the electrode means 3 or 11. The handpiece 6 has a thumb holder 16 and a finger holder 17 to guide the device to the appropriate location of the targeted tissue site.

Figure 2:
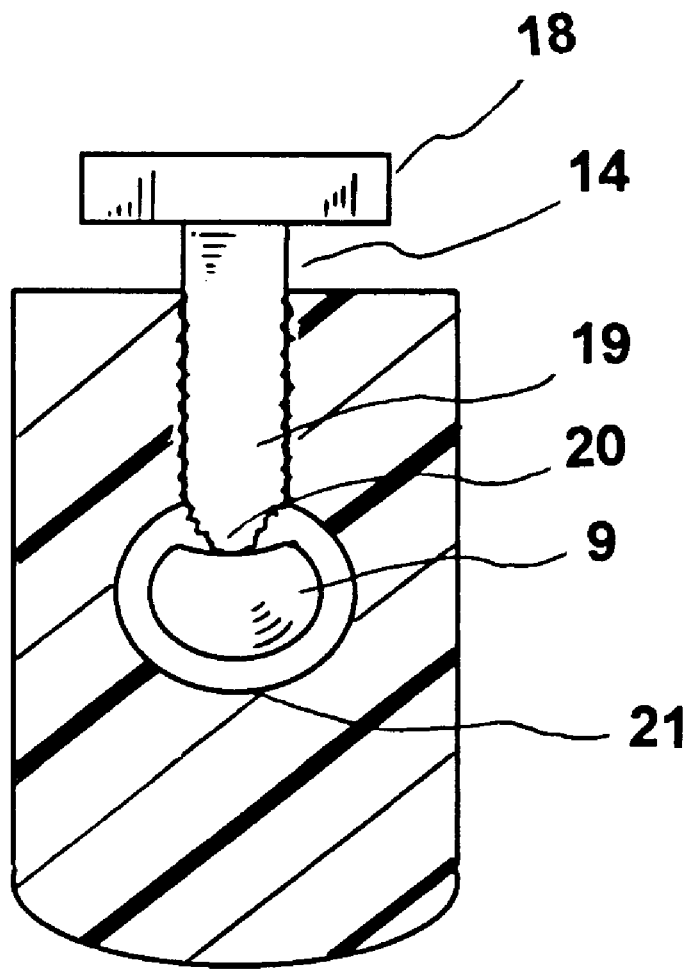
FIG. 2 is a cross-sectional view of the locking means for applying the pressure therapy to the medical device in FIG. 1.

FIG. 2 shows a cross-sectional view of the locking mechanism 14 for applying the pressure therapy to the medical device of the present invention. The locking mechanism 14 comprises a turning knob 18 and a forwarding screw 19, wherein the end 20 of the screw 19 can push the second elongate tubular shaft 9 against the receptacle 21 and lock the shaft in place. By loosening the screw 19, the second elongate tubular shaft 9 can freely move longitudinally, relative to the first elongate tubular shaft 1.

Figure 3:
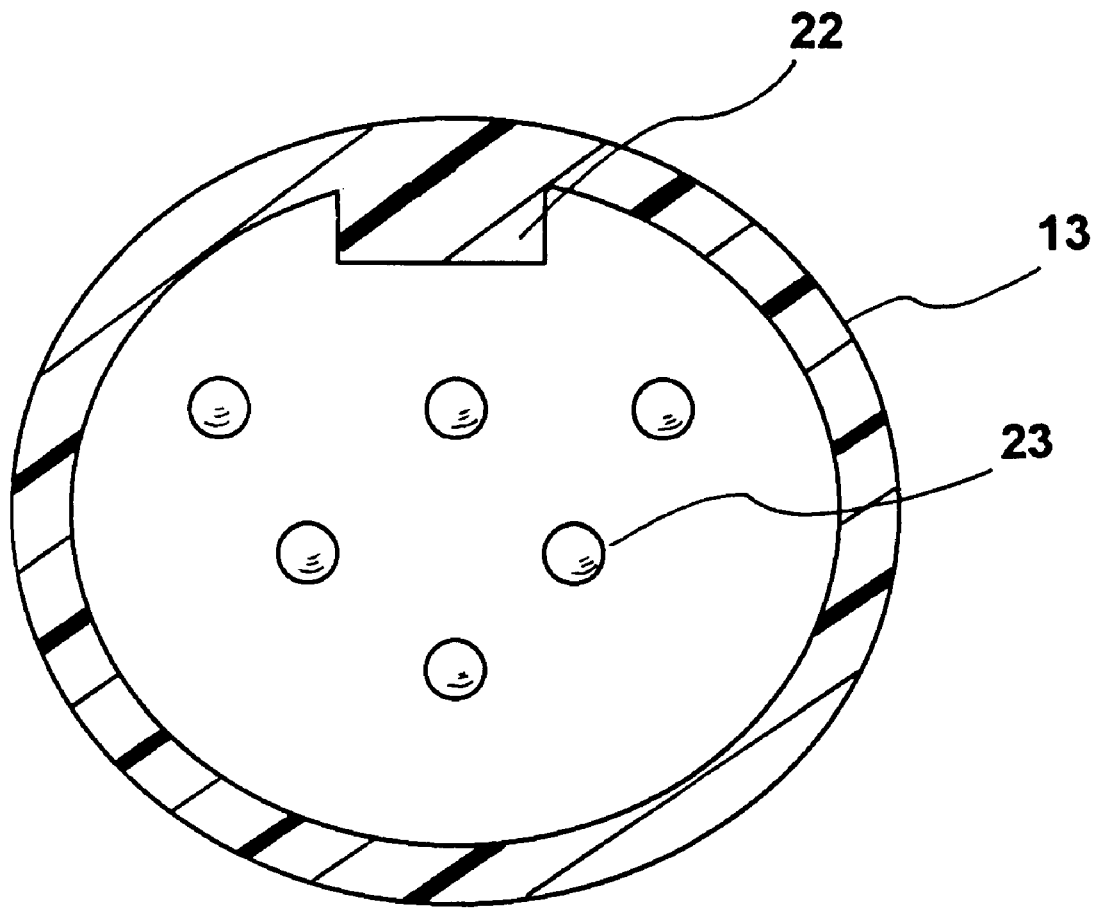
FIG. 3 is a front view of the connector means of FIG. 1.

FIG. 3 shows a front view of the connector means 13 of the present invention. The connector 13 comprises an orientation notch 22 and several pins 23 for connecting the electrical conductors 4 and 12, and temperature sensing wires 24 and 25 to external instruments, such as a RF generator, an EKG monitor, or a temperature control mechanism.

Figure 4:
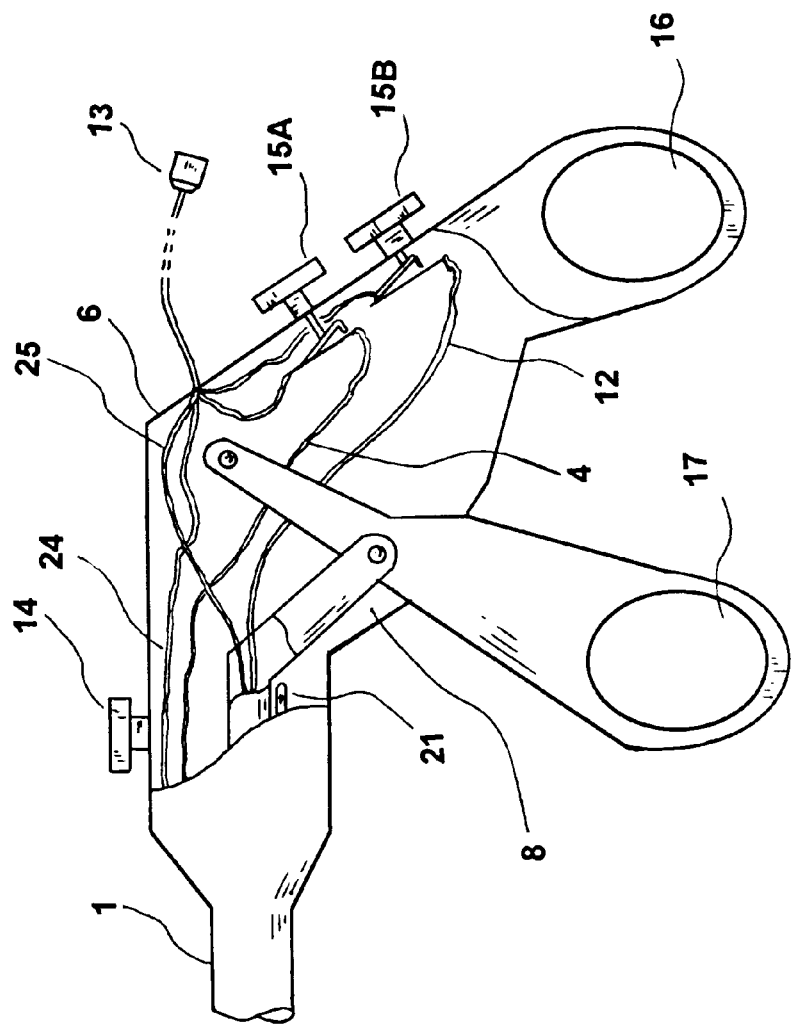
FIG. 4 is a cross-sectional view of the handpiece of FIG. 1.

FIG. 4 shows a cross-sectional view of the handpiece 6 of the present invention. The handpiece 6 comprises a cavity 8, and holders 16 and 17 for the thumb and finger so that the second elongate tubular shaft 9 can move longitudinally relative to the first elongate tubular shaft 1. The electricity of the electrical conductors 4 and 12 are controlled through on-off control knobs 15A and 15B to selectively deliver RF energy to either the first electrode means 3 or the second electrode means 11. The receptacle 21 is secured on the wall of the handpiece 6, which is sued to assist the locking mechanism 14. In one alternate embodiment, either one of the electrode means 3 or 11 is used as the DIP electrode to complete the RF system circuit.

Figure 5:
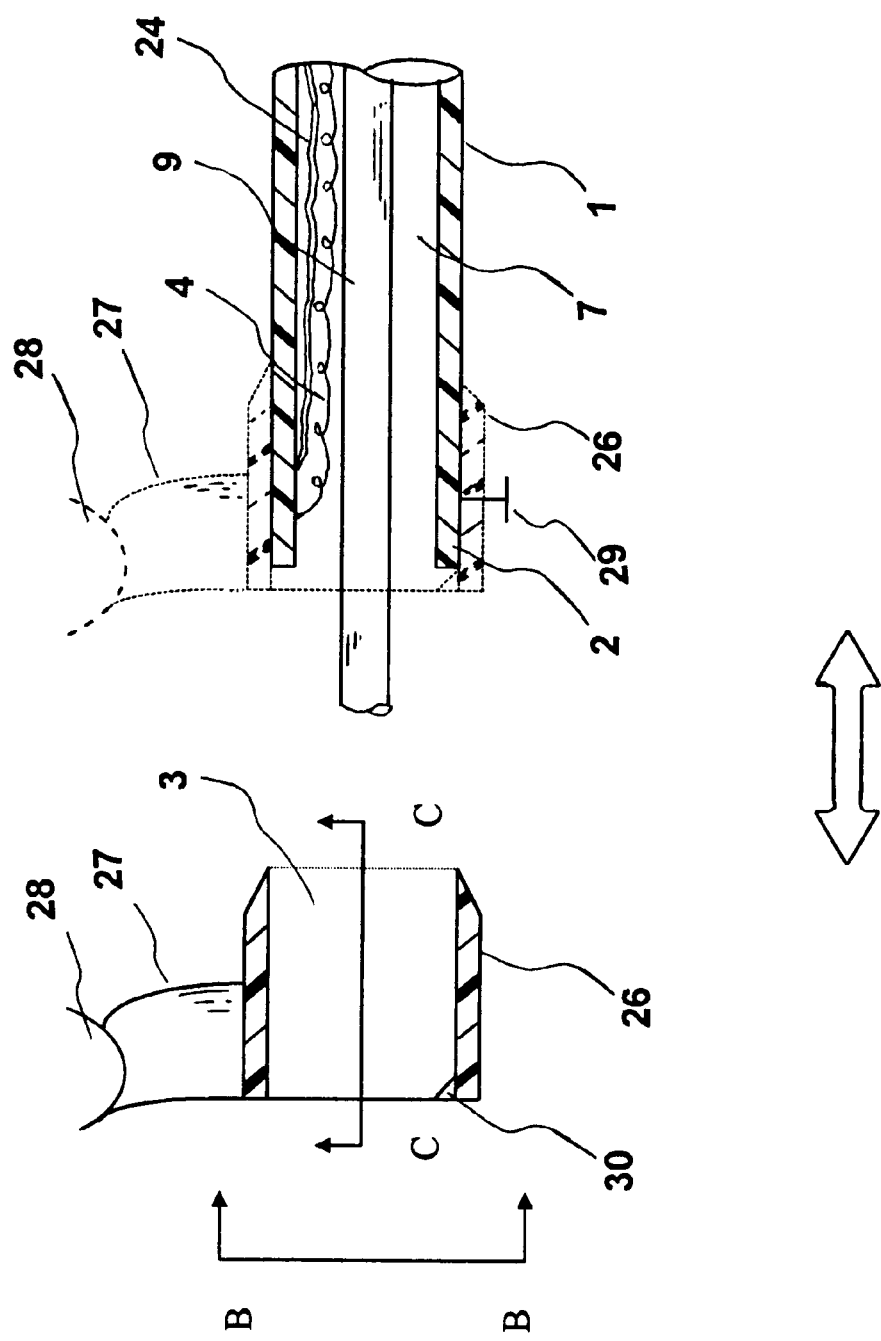
FIG. 5 is a side-view of the mounting means for the first electrode means mounted to a first tubular elongate shaft.

The electrode means 3 is disposed at the distal end portion 2 of the first elongate tubular shaft 1. FIG. 5 shows a side-view of the mounting means for the first electrode means 3 mounted to a first tubular elongate shaft 1. The electrode means 3 comprises a base ring 26, which is non-conductive, a support 27, which is also non-conductive, and a conductive element 28 disposed on the top of the support 27, wherein the base ring 26 is to fit into the distal end portion 2 of the first elongate tubular shaft 1. A stopper 30 at the distal end of the base ring 26 is in place to restrict and position the base ring 26 at the proper location on the shaft 1 when being inserted. The electrical conductor 4 is connected to the conductive element 28. In one embodiment, the surface of the conductive element 28 can be either flat, convex, or concave when facing the second electrode means 11. After fitting the electrode means 3 onto the distal end portion 2, a set screw 29 is used to securely maintain the electrode means 3 in place with respect to the first elongate tubular shaft 1.

FIG. 5A shows the end view B—B of the electrode means 3, while FIG. 5B shows the transverse view C—C of the electrode means 3 in FIG. 5. The electrode means 3 has a stopper 30, a base ring 26, a support 27, and a wire 4 or 24. The base ring 26 has a length of 31 and an inside diameter of 32. A plurality of electrical contacts is located at the inner side of the base ring 26. The contact may include an electrical contact 33 for the electrical conductor 4, and contacts 34 and 35 for thermocouple wires 24. Similarly, there are the same number of electrical contacts (not shown) on the exterior side of the first elongate tubular shaft 1 at the corresponding locations for the electrical conductor and the thermocouple wires.

Figure 6:
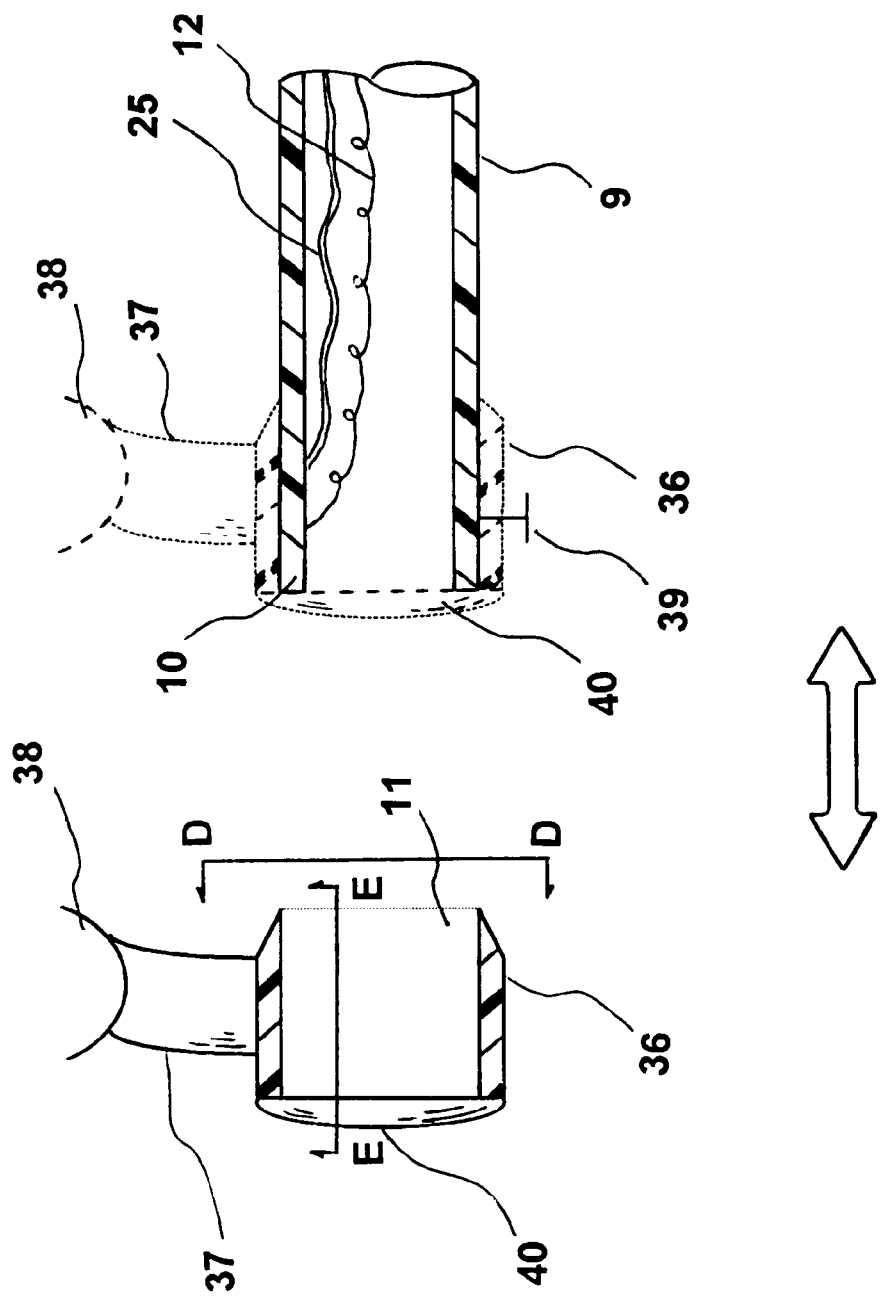
FIG. 6 is a side-view of the mounting means for the second electrode means mounted to a second tubular elongate shaft.

FIG. 6 shows a side-view of the mounting means for the second electrode means 11 mounted to a second tubular elongate shaft 9. The electrode means 11 is disposed at the distal end portion 10 of the second elongate tubular shaft 9. The electrode means 11 comprises a base ring 36, which is non-conductive, a support 37, which is also non-conductive, and a conductive element 38 disposed on the top of the support 37, wherein the base ring 36 is to fit into the distal end portion 10 of the second elongate tubular shaft 9. A stopper 40 at the distal end of the base ring 36 is in place to restrict and position the base ring 36 at the proper location on the shaft 9 when the base ring 36 is inserted. The insulated electrical conductor 12 is connected to the conductive element 38. In one embodiment, the surface of the conductive element 38 can be either flat, convex, or concave when facing the first electrode means 3. After fitting the electrode means 11 onto the distal end portion 10, a set screw 39 is used to securely maintain the electrode means 11 in place with respect to the second elongate tubular shaft 9.

FIG. 6A shows the front view D—D of the electrode means 11, while FIG. 6B shows the transverse view E—E of the electrode means 11 in FIG. 6. The electrode means 11 has a stopper 40, a base ring 36, a support 37 and a wire 12 or 25. The base ring 36 has a length of 41 and an inside diameter of 42. A plurality of electrical contacts is located at the inner side of the base ring 36. The contact may include an electrical contact 43 for the electrical conductor 12, and contacts 44 and 45 for thermocouple wires 25. Similarly, there are the same number of electrical contacts (not shown) on the exterior side of the second elongate tubular shaft 9 at the corresponding locations for the electrical conductor and the thermocouple wires.

In one embodiment, a plurality of temperature sensing means 62 and 63 are disposed close to the electrode means 3 and 11, respectively. Insulated temperature sensor wire means 24 and 25 passes from the temperature sensing means 62 and 63 at the distal end portion, to an external temperature control mechanism through the outlet connector 13. The RF energy delivery is controlled by using the measured temperature from the temperature sensing means 62 and/or 63, through a closed-loop temperature control mechanism and/or algorithm. When the measured temperature rises to the preset high-limit point, the temperature control mechanism sends out a signal to cut off the RF energy supply. In a similar manner, when the measured temperature drops to the preset low-limit point, the temperature control mechanism sends out a signal to activate the RF energy supply.

Figure 7:
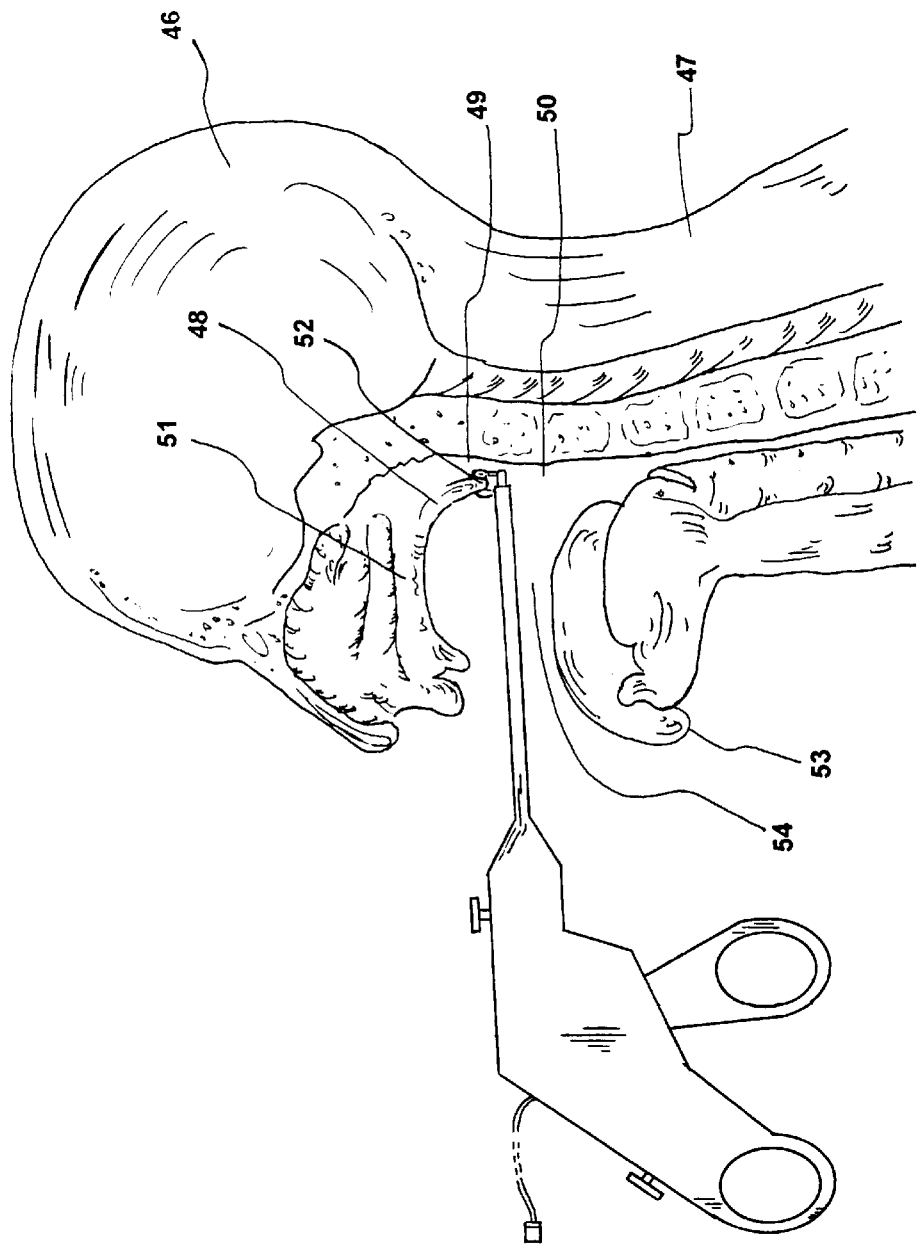
FIG. 7 shows a perspective view of an uvula region being treated by the medical device of the present invention.

FIG. 7 shows a perspective view of an uvula region being treated by the medical device of the present invention. For illustrative purposes, the median section of the head 46 and the neck region 47 is shown in FIG. 7. The soft palate 48 is a shelf of soft tissue which lies between the nasopharynx 49 and the oropharynx 50. It is attached in front to the posterior margin of the hard palate 51 and on either side to the deep surface of the superior constrictor muscles. Its posterior margin is free, and from its central part a conical process, called the uvula 52, hangs downwards. When the muscles of the soft palate are relaxed, the soft palate inclines downwards and backwards and is positioned concave downwards in both the coronal and sagital planes. During procedures, the tongue 53 is pulled down to open the oral cavity 54. A tissue treatment method for reducing the size and mass of cellular tissues of the uvula in order to reduce snoring comprises the steps of: (a) inserting a medical device into the uvula of a patient, wherein the medical device comprises a first elongate tubular shaft, on which, thereof a first electrode means is mounted on a distal end portion, an electrical conductor passing through the shaft and connected to the first electrode means, and mounted on a proximal end portion of the shaft to a handpiece of the device, wherein the first elongate tubular shaft has at least a lumen extending between the distal end portion and the proximal end portion, and wherein the handpiece has a cavity; a second elongate tubular shaft located within the lumen of the first elongate tubular shaft, the second elongate tubular shaft, on which, thereof a second electrode means is mounted on a distal end portion, an electrical conductor passing through the shaft and connected to the second electrode means, and mounted on a proximal end portion of the shaft to the handpiece of the device, wherein the second elongate tubular shaft is moveable axially, relative to the first elongate tubular shaft; and a RF energy generating means, wherein the RF energy is supplied to either the first electrode means, the second electrode means, or to both electrode means through electrical conductors; (b) contacting the two electrode means of the medical device against the cellular tissues of the uvula of a patient from its opposite sides; and (c) applying RF energy to the tissues surrounding the exposed electrode area to effect treatment of the uvula tissues.

As an alternative illustration, a method of treating the polyp of a patient, the method comprises the steps of: (a) placing a medical device against a polyp of the patient, wherein the medical device comprises a first elongate tubular shaft, on which, thereof a first electrode means is mounted on a distal end portion, an electrical conductor passing through the shaft and connected to the first electrode means, and mounted on a proximal end portion of the shaft to a handpiece of the device, wherein the first elongate tubular shaft has at least a lumen extending between the distal end portion and the proximal end portion, and wherein the handpiece has a cavity; a second elongate tubular shaft located within the lumen of the first elongate tubular shaft, the second elongate tubular shaft, on which, thereof a second electrode means is mounted on a distal end portion, an electrical conductor passing through the shaft and connected to the second electrode means, and mounted on a proximal end portion of the shaft to the handpiece of the device, wherein the second elongate tubular shaft is moveable axially relative to the first elongate tubular shaft; and a RF energy generating means, wherein the RF energy is supplied to either the first electrode means, the second electrode means, or to both electrode means through electrical conductors; (b) contacting the two electrode means of the medical device against the polyp of the patient from its opposite sides; and (c) applying RF energy to the tissues surrounding the exposed electrode area to effect treatment of the polyp.

Figure 8:
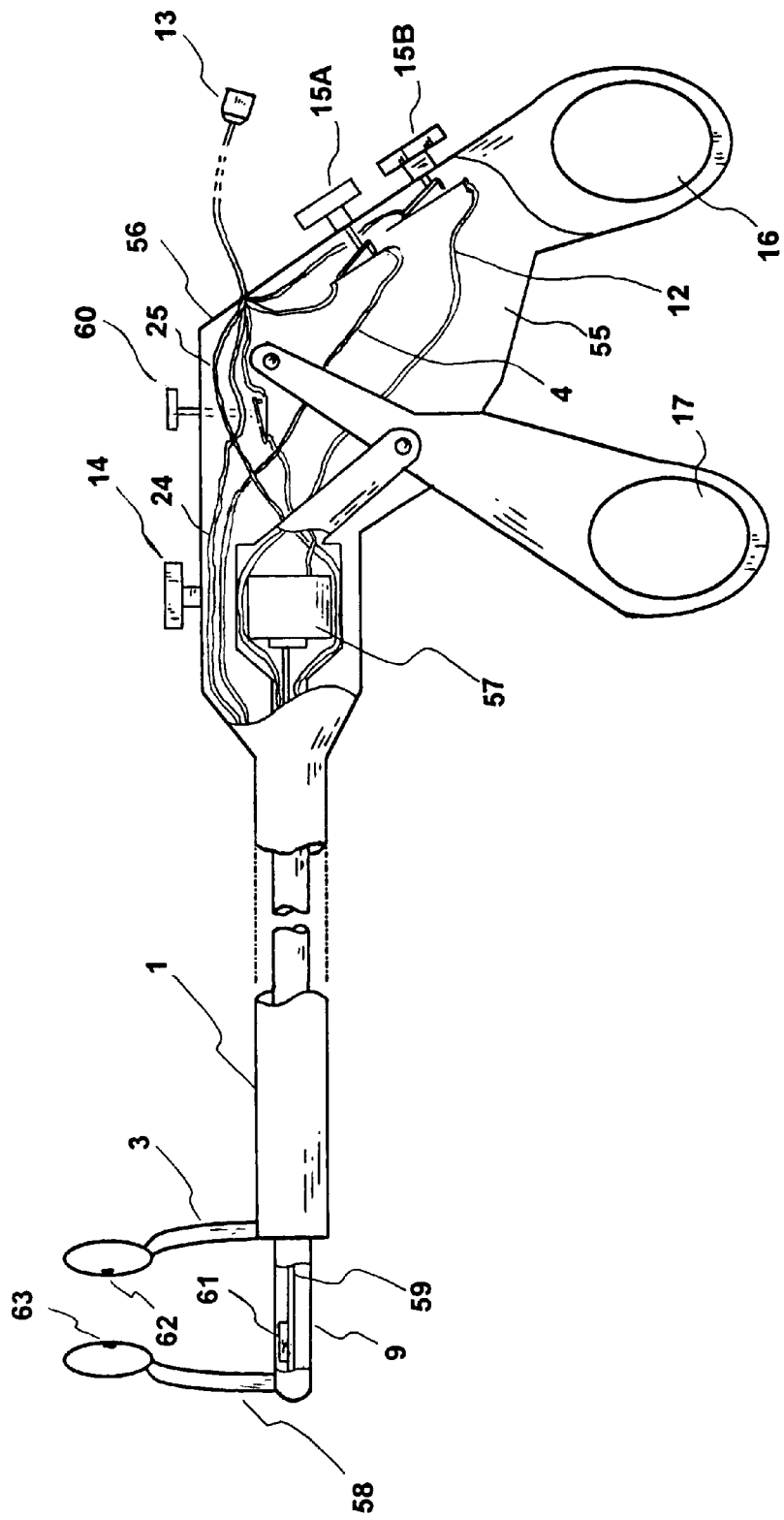
FIG. 8 is an over-all view of the medical device, having a plurality of electrode means, a clamp-type fixture, and an electric vibration means, constructed in accordance with the principles of the present invention.

FIG. 8 shows an over-all view of the medical device, having a plurality of electrode means, a clamp-type fixture, and an electric vibration means, constructed in accordance with the principles of the present invention. In addition to the above-described medical device, there is a cavity 55 inside the handpiece 56, in which a motor 57 is located. The second electrode means 58 which is mounted at the distal end portion of the second elongate tubular shaft 9 is connected to the handpiece 56 by a shaft 59. In one embodiment, a battery means (not shown), which is located at the proximal end of the cavity 55 of the handpiece 56, is used to supply the energy to the motor 59. In an alternate embodiment, the motor 59 is powered by an alternate current (AC) through a power input plug (not shown). In either case, the power supply is controlled by an on-off switch button 60 located conveniently on the handpiece 56. This alternate device has the electrical conductors and temperature sensing wires as described in the above-described embodiment.

Attached to the shaft 59 there is an eccentric weight 61. The eccentric rotation of the weight 61 places the electrode means 58 into vibration via the shaft 59 due to the unbalancing effect of the eccentric weight 61. The vibrational amplitude of the electrode means 58 of the second elongate tubular shaft 9 is determined by the geometry of the shaft 59, the mass and configuration of the weight 61, and the rotational speed of the motor 57, among other factors.

The external RF energy generator means has the capability to supply RF energy by controlling the time, power, and temperature through an optional separate closed-loop temperature control means. The patient is connected to the RF generator means through a DIP electrode to form a closed-loop current system. Therefore, RF energy is applied and delivered to the targeted uvula region, through the electrode means of this invention. The radiofrequency energy current in this invention is preferably within the range of 50 to 2,000 kHz. The frequency of the vibration of the medical device in this invention is preferably within the range of 60 to 1000 cycles per minute. By simultaneously applying RF energy to the electrode and by applying the pressure therapy, the uvula can be treated.

In a particular embodiment, the material for the electrode means of this invention consists of conductive metals such as platinum, iridium, gold, silver, stainless steel, Nitinol, or an alloy of these metals.

From the foregoing description, it should now be appreciated that a device system for the uvula and the treatment of tissues, comprising a suitable energy source and a pressure therapy, with an optional vibrational massage therapy has been disclosed. While the invention has been described with reference to a specific embodiment, the description is illustrative of the invention and is not to be construed as limiting the invention. Various modifications and applications may occur to those who are skilled in the art, without departing from the true spirit and scope of the invention, as described by the appended claims.

What is claimed is:

1. A medical device comprising:
    a first elongate tubular shaft, on which, thereof a first electrode means is mounted on a distal end portion, an electrical conductor passing through the shaft and connected to the first electrode means, and mounted on a proximal end portion of the shaft to a handpiece of the device, wherein the first elongate tubular shaft has at least a lumen extending between the distal end portion and the proximal end portion, and wherein the handpiece has a cavity;
    said first electrode means comprises a base ring, a support, a conductive element, a set screw, and a stopper;
    a second elongate tubular shaft located within the lumen of the first elongate tubular shaft, the second elongate tubular shaft, on which, thereof a second electrode means is mounted on a distal end portion, an electrical conductor passing through the shaft and connected to the second electrode means, and mounted on a proximal end portion of the shaft to the handpiece of the device, wherein the second elongate tubular shaft is moveable longitudinally relative to the first elongate tubular shaft;
    the distal end portion of the first elongate tubular shaft comprising a first detachable mounting means for mounting the first electrode means to the first elongate tubular shaft of the medical device and the distal end portion of the second elongate tubular shaft comprising a second detachable mounting means for mounting the second electrode means to the second elongate tubular shaft of the medical device;
    said first mounting means comprising the base ring shaped for attachment to the distal end portion of the first elongate tubular shaft, the stopper to restrict and position the base ring onto the distal end portion of the shaft, and the set screw to lock the electrode means in place;
    a locking mechanism disposed on the handpiece, wherein the longitudinal location of the second elongate tubular shaft relative to the first elongate tubular shaft is determined and locked in; and
    a connector means attached to the handpiece, wherein electricity from an external electrical source is relayed to the electrical conductors through the conductor means.

2. The medical device of claim 1, wherein the second electrode means comprises a base ring, a support, a conductive element, a set screw, and a stopper, and wherein said second mounting means comprises the base ring shaped for attachment to the distal end portion of the second elongate tubular shaft, the stopper to restrict and position the base ring onto the distal end portion of the shaft, and the set screw to lock the electrode means in place.

3. The medical device as in claim 2 further comprising means for generating vibration at the distal end portion of the second elongate tubular shaft, wherein the means for generating vibration at the distal end portion comprises a motor mounted in the cavity of the handpiece, which has a rotatable motor shaft, an elongate connecting shaft having a first end to which the distal end portion is connected, and a second end connected to the handpiece, a weight eccentrically mounted on the motor shaft with respect to the motor shaft axis, so as to rotate eccentrically, so that when the motor shaft rotates, the distal end portion of the second elongate tubular shaft vibrates.

4. The medical device of claim 3, wherein the frequency of the vibration is within the range of 60 to 1000 cycles per minute.

5. A method of treating the polyp of a patient, the method comprising:

(a) placing a medical device against a polyp of the patient, wherein the medical device comprises a first elongate tubular shaft, on which, thereof a first electrode means is mounted on a distal end portion, an electrical conductor passing through the shaft and connected to the first electrode means, and mounted on a proximal end portion of the shaft to a handpiece of the device, wherein the first elongate tubular shaft has at least a lumen extending between the distal end portion and the proximal end portion, and wherein the handpiece has a cavity; a second elongate tubular shaft located within the lumen of the first elongate tubular shaft, the second elongate tubular shaft, on which, thereof a second electrode means is mounted on a distal end portion, an electrical conductor passing through the shaft and connected to the second electrode means, and mounted on a proximal end portion of the shaft to the handpiece of the device, wherein the second elongate tubular shaft is moveable, axially, relative to the first elongate tubular shaft; the distal end portion of the first elongate tubular shaft comprising a detachable mounting means for mounting the first electrode means to the first elongate tubular shaft of the medical device and the distal end portion of the second elongate tubular shaft comprising a detachable mounting means for mounting the second electrode means to the second elongate tubular shaft of the medical device; a RF energy generating means, wherein the RF energy is supplied to either the first electrode means, the second electrode means, or to both electrode means through the electrical conductors; means for generating vibration at the distal end portion of the second elongate tubular shaft, wherein the means for generating vibration at the distal end portion comprises a motor mounted in the cavity of the handpiece, which has a rotatable motor shaft, an elongate connecting shaft having a first end to which the distal end portion is connected, and a second end connected to the handpiece, a weight eccentrically mounted on the motor shaft with respect to the motor shaft axis, so as to rotate eccentrically, so that when the motor shaft rotates, the distal end portion of the second elongate tubular shaft vibrates;

(b) contacting the two electrode means of the medical device against the polyp of the patient from its opposite sides; and (c) applying RF energy to the tissues surrounding the exposed electrode area to effect treatment of the polyp.

6. The treatment method as in claim 5 further comprising initiating the vibration to the distal section of the device to effect the vibrational therapeutic massage for the polyp tissues.

7. A tissue treatment method for reducing the size and mass of cellular tissues of the uvula in order to reduce snoring comprising the steps of:

(a) inserting a medical device into the uvula of a patient, wherein the medical device comprises a first elongate tubular shaft, on which, thereof a first electrode means is mounted on a distal end portion, an electrical conductor passing through the shaft and connected to the first electrode means, and mounted on a proximal end portion of the shaft to a handpiece of the device, wherein the first elongate tubular shaft has at least a lumen extending between the distal end portion and the proximal end portion, and wherein the handpiece has a cavity; a second elongate tubular shaft located within the lumen of the first elongate tubular shaft, the second elongate tubular shaft, on which, thereof a second electrode means is mounted on a distal end portion, an electrical conductor passing through the shaft and connected to the second electrode means, and mounted on a proximal end portion of the shaft to the handpiece of the device, wherein the second elongate tubular shaft is moveable, axially, relative to the first elongate tubular shaft; and a RF energy generating means, wherein the RF energy is supplied to either the first electrode means, the second electrode means, or to both electrode means through electrical conductors;

(b) contacting the two electrode means of the medical device against the cellular tissues of the uvula of a patient from its opposite sides; and (c) applying RF energy to the tissues surrounding the exposed electrode area to effect treatment of the uvula tissues.

8. The treatment method as in claim 7 further comprising means for generating vibration at the distal end portion of the second elongate tubular shaft, wherein the means for generating vibration at the distal end portion comprises a motor mounted in the cavity of the handpiece, which has a rotatable motor shaft, an elongate connecting shaft having a first end to which the distal end portion is connected, and a second end connected to the handpiece, a weight eccentrically mounted on the motor shaft with respect to the motor shaft axis, so as to rotate eccentrically, so that when the motor shaft rotates, the distal end portion of the second elongate tubular shaft vibrates.

9. The treatment method of claim 8, further comprising initiating the vibration to the distal section of the device to effect the vibrational therapeutic massage for the uvula tissues.

10. The medical device as in claim 7 further comprising at least one temperature sensor, wherein the temperature sensor is disposed at the electrode means of the first and/or the second elongate tubular shafts.

* * * * *